United States Patent
Russell et al.

(10) Patent No.: US 11,280,779 B2
(45) Date of Patent: Mar. 22, 2022

(54) SOLVENCY FOR ASPHALTENE DEPOSIT REMEDIATION OR INHIBITION

(71) Applicant: ChampionX USA Inc., Sugar Land, TX (US)

(72) Inventors: Christopher Alexander Russell, Sugar Land, TX (US); Emily Teresa Pohl, Pearland, TX (US)

(73) Assignee: ChampionX USA Inc., Sugar Land, TX (US)

( * ) Notice: Subject to any disclaimer, the term of this patent is extended or adjusted under 35 U.S.C. 154(b) by 496 days.

(21) Appl. No.: 16/224,290

(22) Filed: Dec. 18, 2018

(65) Prior Publication Data

US 2019/0187120 A1     Jun. 20, 2019

Related U.S. Application Data

(60) Provisional application No. 62/607,102, filed on Dec. 18, 2017.

(51) Int. Cl.
| | |
|---|---|
| *G01N 33/28* | (2006.01) |
| *G01N 15/08* | (2006.01) |
| *B01D 21/01* | (2006.01) |
| *C09K 8/524* | (2006.01) |
| *G01N 31/16* | (2006.01) |

(52) U.S. Cl.
CPC ......... *G01N 33/2823* (2013.01); *B01D 21/01* (2013.01); *C09K 8/524* (2013.01); *G01N 15/088* (2013.01); *B01D 2252/205* (2013.01); *B01D 2257/7027* (2013.01); *G01N 31/162* (2013.01)

(58) Field of Classification Search
None
See application file for complete search history.

(56) References Cited

U.S. PATENT DOCUMENTS

| | | | |
|---|---|---|---|
| 3,261,774 | A | 7/1966 | Newkirk et al. |
| 4,910,999 | A | 3/1990 | Eaton |
| 5,156,975 | A | 10/1992 | Nelson |
| 5,391,632 | A | 2/1995 | Krull et al. |
| 6,313,367 | B1 | 11/2001 | Breen |
| 7,736,900 | B2 | 6/2010 | Pauli et al. |

(Continued)

FOREIGN PATENT DOCUMENTS

| | | |
|---|---|---|
| WO | 01/38459 A1 | 5/2001 |
| WO | 2012/121804 A1 | 9/2012 |

(Continued)

OTHER PUBLICATIONS

Miknis, Francis P. et al., NMR imaging studies of asphaltene precipitation in asphalts, Fuel, vol. 77, No. 5, pp. 399-405 (1998).

(Continued)

*Primary Examiner* — Jeffrey D Washville
(74) *Attorney, Agent, or Firm* — Stinson LLP (57) ABSTRACT

Methods for estimating the solvency potential for various chemical additives used for asphaltene deposit remediation or inhibition have been developed. These methods can be used for remediating or inhibiting asphaltene deposition in various applications including upstream production (e.g., near-wellbore, downhole, flow-lines, separators), midstream processes (e.g., pipe lines, transport, and storage), and downstream (e.g., hydrocarbon refining).

20 Claims, 2 Drawing Sheets

(56) References Cited

U.S. PATENT DOCUMENTS

| | | |
|---|---|---|
| 2004/0163995 A1 | 8/2004 | Cornelisse |
| 2005/0070443 A1 | 3/2005 | Madachik, Jr. |
| 2006/0156820 A1 | 7/2006 | Jones et al. |
| 2007/0100082 A1 | 5/2007 | Dickakian et al. |
| 2008/0016755 A1 | 1/2008 | Siggelkow et al. |
| 2009/0114394 A1 | 5/2009 | Javora et al. |
| 2012/0125087 A1 | 5/2012 | Sandu et al. |
| 2014/0260567 A1 | 9/2014 | Fouchard et al. |
| 2015/0102224 A1* | 4/2015 | Respini ............ G01N 21/274 250/341.1 |
| 2015/0112060 A1 | 4/2015 | Hernandez Altamirano et al. |
| 2015/0219614 A1 | 8/2015 | Respini et al. |
| 2015/0225655 A1 | 8/2015 | Adams et al. |
| 2016/0298039 A1 | 10/2016 | Falkler et al. |
| 2016/0355629 A1 | 12/2016 | Deshpande et al. |
| 2017/0003264 A1 | 1/2017 | Adams et al. |
| 2017/0023485 A1* | 1/2017 | Stubbins ............ G01N 21/3577 |

FOREIGN PATENT DOCUMENTS

| | | |
|---|---|---|
| WO | 2014/116508 A1 | 7/2014 |
| WO | 2015/175432 A1 | 11/2015 |
| WO | 2015/176007 A1 | 11/2015 |

OTHER PUBLICATIONS

Wiehe, Irwin A. et al., Design of Synthetic Dispersants for Asphaltenes, Petroleum Science and Technology, vol. 21, No. 3-4, (2003) pp. 527-536.

Spiecker, P. Matthew et al., Effects of petroleum resins on asphaltene aggregation and water-in-oil emulsion formation, Colloids and Surfaces A: Physicochem. Eng. Aspects, vol. 220, No. 1-3 (2003) pp. 9-27.

Invitation to Pay Additional Fees and, Where Applicable, Protect Fee dated Apr. 17, 2019 relating to PCT Patent Application No. PCT/US2018/066249, 6 pages.

Chandio et al., Temperature effects on solubility of asphaltenes in crude oils, Chemical Engineering Research and Design 94 (2015) pp. 573-583.

Gharfeh et al., A General Study of Asphaltene Flocculation Prediction at Field Conditions, SPE Production & Dperations (Aug. 2007), pp. 277-284.

Kashefi et al., Investigation of the performance of several chemical additives on inhibition of asphaltene precipitation, Energy Sources, Part A: Recovery, Utilization, and Environmental Effects (2016), vol. 38, No. 24, pp. 3647-3652.

Nedelchev et al., Visbreaker Performance Improvement by Optimisation of Process Conditions and Application of Chemical Additive Treatment Program, Oil Gas European Magazine (2013), pp. OG1-OG7.

Tiwari et al., In-Situ Heat Generation for Near Wellbore Asphaltene and Wax Remediation, International Petroleum Technology Conference (IPTC 17681) (2014), pp. 1-9.

* cited by examiner

SOLVENCY FOR ASPHALTENE DEPOSIT REMEDIATION OR INHIBITION

CROSS REFERENCE TO RELATED APPLICATIONS

This application claims priority to U.S. Provisional Patent Application Ser. No. 62/607,102 filed on Dec. 18, 2017, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Methods for estimating the solvency potential for various chemical additives used for asphaltene deposit remediation or inhibition have been developed. These methods can be used for remediating or inhibiting asphaltene deposition in various applications including upstream production (e.g., near-wellbore, downhole, flow-lines, separators), midstream processes (e.g., pipe lines, transport, and storage), and downstream (e.g., hydrocarbon refining).

BACKGROUND OF THE INVENTION

Crude oils include the solubility fractions of maltenes and asphaltenes. Maltenes constitute the fraction of oil that is soluble in low molecular mass n-alkane solvents, such as n-pentane, n-hexane, and n-heptane. Asphaltenes are defined as the crude oil fraction that is soluble in aromatic solvents and insoluble in low-boiling straight chain alkanes. Asphaltene molecules have complex structures and are typically polar molecules with relatively high molecular weights (approximately 700 to 1,000 g/mole). Asphaltenes can contain carbon, hydrogen, nitrogen, oxygen, and sulfur, as well as trace amounts of vanadium and nickel.

Asphaltenes are typically stable under original reservoir conditions, but can be destabilized and precipitate from crude oil during production due to changes in temperature, pressure, chemical composition, and shear rate. Asphaltene deposits can occur throughout the production system, from inside the reservoir formation to pumps, tubing, wellheads, safety valves, flow lines, and surface facilities used in the extraction process. Asphaltene deposits can cause production rate decline and other operational problems, such as increased fluid viscosity and density, and stabilization of oil-water emulsions. The nature of asphaltene deposits, which can appear hard and coal-like or sticky and tar-like, is determined by the composition of the crude oil and the conditions under which precipitation occurred.

Current remediation technologies for asphaltene deposits in the oilfield environment can involve physical and chemical aspects. The deposit, blockage, or obstruction, can be moved by physical force. However, this is often a very expensive operation, and can cause significant loss in production. Chemical methods are relatively less time and cost prohibitive, and typically involve a solvent soak coupled with the addition of an active component to mobilize and solubilize, thereby allowing removal of the deposit. Thus, chemical treatment with additives such as dispersants and inhibitors is one of the commonly adopted control options for the remediation and prevention of asphaltene deposition.

However, although the chemical treatment strategy is frequently used, the criteria behind the product selection are often limited to anecdotal evidence and subjective laboratory bottle tests. Thus, an improved method for the selection of chemical agents for removing or inhibiting asphaltene deposits in oil production and processing is still needed.

Therefore, a need exists for a faster, more efficient method to determine the agents that perform advantageously with a particular crude oil.

BRIEF SUMMARY OF THE INVENTION

Various methods are disclosed herein including a method for determining a stability of an asphaltene dispersion. The method comprises contacting a first measured amount of a solid asphaltene-containing deposit with a first measured amount of a solvating agent and a first measured amount of an aromatic hydrocarbon solvent to form a first test sample; and contacting a second measured amount of the solid asphaltene-containing deposit with a second measured amount of the solvating agent and a second measured amount of the aromatic hydrocarbon solvent to form a second test sample. The solid asphaltene-containing deposit is allowed to dissolve in the solvating agent and aromatic hydrocarbon solvent to form a solution in the first and second test samples. A first measured amount of an aliphatic hydrocarbon solvent is added to the first test sample until a first asphaltene flocculant forms; and a second measured amount of the aliphatic hydrocarbon solvent is added to the second test sample until a second asphaltene flocculant forms. A solvency factor, an asphaltene factor, and a solubility value is calculated from the first and second measured amounts of the aromatic hydrocarbon solvent and the first and second measured amounts of the aliphatic hydrocarbon solvent. Optionally, when the first or second asphaltene flocculant does not form, a concentration of the solid asphaltene-containing deposit in the first and second test samples is altered thereby allowing a first and second asphaltene flocculant to form.

Additionally, disclosed herein is a method for determining a stability of an asphaltene dispersion. The method comprises dissolving a measured amount of a solid asphaltene-containing deposit in a first solvent to form an asphaltene sample, and contacting a first measured amount of the asphaltene sample with a first measured amount of an aromatic hydrocarbon solvent to form a first test sample. A second measured amount of the asphaltene sample is collected and optionally contacted with a second measured amount of the aromatic hydrocarbon solvent to form a second test sample. A first measured amount of an aliphatic hydrocarbon solvent is added to the first test sample until an asphaltene flocculant forms. A second measured amount of the aliphatic hydrocarbon solvent is added to the second test sample until an asphaltene flocculant forms. A solvency factor, an asphaltene factor, and a solubility value is calculated from the first and second measured amounts of the aromatic hydrocarbon solvent and the first and second measured amounts of the aliphatic hydrocarbon solvent. The steps herein are repeated upon adding a solvating agent to the first and second test samples and the solubility value of the samples is compared with the solvating agent to the solubility value of the test samples without the solvating agent. Optionally, when the first or second asphaltene flocculant does not form, a concentration of the solid asphaltene-containing deposit in the first and second test samples is altered to form a first and second asphaltene flocculant.

Further, methods described herein can have the aromatic hydrocarbon solvent comprise toluene, xylene, heavy aromatic distillates, methyl naphthalene, or a combination thereof. Preferably, the aromatic hydrocarbon solvent comprises toluene.

The methods described herein can have the aliphatic hydrocarbon solvent comprises and n-alkane. In particular, the aliphatic hydrocarbon solvent comprises n-pentane, n-hexane, n-heptane, n-octane, iso-octane, nonane, decane, undecane, dodecane, pentadecane, hexadecane, or a combination thereof. Preferably, the aliphatic hydrocarbon solvent comprises iso-octane.

The methods described herein can have the first solvent comprise a mixture of an aliphatic solvent and an aromatic solvent. The aliphatic solvent in the mixture can be n-pentane, n-hexane, n-heptane, n-octane, iso-octane, nonane, decane, undecane, dodecane, pentadecane, hexadecane, or a combination thereof. The aromatic solvent in the mixture can be toluene, xylene, heavy aromatic distillates, methyl naphthalene, or a combination thereof. Preferably, the first solvent comprises n-heptane and toluene.

The methods disclosed herein can have the ratio of the concentration of the solid asphaltene-containing deposit to the solvating agent be from about 1:4 to about 4:1, from about 1:3 to about 3:1, from about 1:2 to about 2:1, from about 1:1.5 to about 1.5:1, or about 1:1. Preferably, the ratio of the concentration of the solid asphaltene-containing deposit to the solvating agent is about 1:1.

The methods disclosed herein can have the weight ratio of concentrations of the solid asphaltene-containing deposit to the aromatic hydrocarbon solvent be from about 1:8 to about 2:1, from about 1:6 to about 2:1, from about 1:5 to about 2:1, from about 1:4 to about 2:1, from about 1:2 to about 2:1, from about 1:8 to about 1:1, from about 1:6 to about 1:1, from about 1:5 to about 1:1, from about 1:4 to about 1:1, from about 1:2 to about 1:1, 1:8 to about 1:2, from about 1:6 to about 1:2, from about 1:5 to about 1:2, from about 1:4 to about 1:2, or from about 1:3 to about 1:2.

The methods described herein can have the concentration of the solid asphaltene-containing deposit be from about 0.1 wt. % to about 50 wt. %, from about 0.1 wt. % to about 40 wt. %, from about 0.1 wt. % to about 30 wt. %, from about 0.1 wt. % to about 20 wt. %, from about 0.1 wt. % to about 15 wt. %, from about 0.25 wt. % to about 50 wt. %, from about 0.25 wt. % to about 40 wt. %, from about 0.25 wt. % to about 30 wt. %, from about 0.25 wt. % to about 20 wt. %, from about 0.25 wt. % to about 15 wt. %, from about 0.5 wt. % to about 50 wt. %, from about 0.5 wt. % to about 40 wt. %, from about 0.5 wt. % to about 30 wt. %, from about 0.5 wt. % to about 20 wt. %, or from about 0.5 wt. % to about 15 wt. % in the amphiphilic solvent, based on the total weight of the solid asphaltene-containing deposit and the amphiphilic solvent. Preferably, the concentration of the solid asphaltene-containing deposit is from about 5 wt. % to about 10 wt. % in the amphiphilic solvent.

The methods disclosed herein can have the ratio of the concentrations of the asphaltene sample to the aromatic solvent is from about 20:1 to about 1:1.

The methods described herein can also have the second test sample comprise the second measured amount of the asphaltene sample.

The methods can further have the second test sample comprise the second measured amount of the asphaltene sample and a second measured amount of the aromatic hydrocarbon solvent.

The methods disclosed herein can have the asphaltene flocculant be detected by a decrease in light transmission through the test sample.

The methods further can require that when the first asphaltene flocculant is not detected after addition of the aliphatic solvent, the concentration of the asphaltene-containing deposit in the first test sample is increased.

Additionally, the methods can require that when the second asphaltene flocculant is not detected after addition of the aliphatic solvent, the concentration of the asphaltene-containing deposit in the second test sample is increased.

Other objects and features will be in part apparent and in part pointed out hereinafter.

BRIEF DESCRIPTION OF THE SEVERAL VIEWS OF THE DRAWING

Corresponding reference characters indicate corresponding parts throughout the drawings.

DETAILED DESCRIPTION OF THE INVENTION

Deposition of various solids from oil field fluids during production can cause wide ranging flow assurance issues. These issues can have significant economic and safety implications. One common deposit type is an asphaltene material, which is a class of crude oil compounds defined by solubility. It is difficult to determine an effective agent for solvating the asphaltenes in various crude oils. Thus, the methods described herein provide a faster, more efficient method to rank various asphaltene solvating agents using the quantitative results obtained from these methods.

Generally, oil stability or the tendency of various fractions of the oil to deposit, can be described by flocculation ratio and solvency power of a maltene component in the oil. Various methods can use a stability analyzer that provides the relative stability of asphaltenes in petroleum samples. In the methods described herein, a stability analyzer is used to quantify the effect of particular solvating agents on the asphaltene stability and/or tendency to deposit in a particular petroleum sample.

Routine operation involves the preparation of two dilutions of oil in toluene, a low and high concentration. These solutions are well dissolved and mixed with the aid of heat. Once thoroughly mixed and dissolution is complete, the solutions are titrated with an n-alkane solvent at a known delivery rate. Solubility dynamics within the solution are monitored using an optical transmission probe. Transmission increases with titration as dispersion forces increase together with attractive forces, until a point where the attractive forces exceed the dispersion forces and the asphaltene material flocculates and precipitates. When the asphaltene material flocculates and precipitates, the light transmission dramatically decreases. The flocculation points are different for each initial dilution, and from this data, the overall stability of the sample can be obtained. As the process severity in the thermal conversion unit increases, the difference between the solvency factor of the oil (Sf) and asphaltene factor (Af) decreases, and at a solubility value (Sf/Af) of 1.0, complete destabilization is obtained. For the refinery operation, values must be kept far above 1.0, to maintain flow of the petroleum stream and optimize processing efficiency.

It is these features of the test that are amenable to the characterization of oil field asphaltene deposits. The methodology was modified by making up the initial oil sample by mixing one part deposit to one part chemical product, and then making two dilutions in toluene. The resulting solubility parameters provide a semi-quantitative measure of asphaltene solubility in terms of the asphaltene factor (Af), and chemical product solvency power in terms of the solvency factor (Sf). For the example data in FIG. 1, the solvency factor (Sf) and the asphaltene factor (Af) change depending on the solvent dispersant combination, resulting in modification to the overall stability value during the screening process.

Various methods are disclosed herein including a method for determining a stability of an asphaltene dispersion. The method comprises contacting a first measured amount of a solid asphaltene-containing deposit with a first measured amount of a solvating agent and a first measured amount of an aromatic hydrocarbon solvent to form a first test sample; and contacting a second measured amount of the solid asphaltene-containing deposit with a second measured amount of the solvating agent and a second measured amount of the aromatic hydrocarbon solvent to form a second test sample. The solid asphaltene-containing deposit is allowed to dissolve in the solvating agent and aromatic hydrocarbon solvent to form a solution in the first and second test samples. A first measured amount of an aliphatic hydrocarbon solvent is added to the first test sample until a first asphaltene flocculant forms; and a second measured amount of the aliphatic hydrocarbon solvent is added to the second test sample until a second asphaltene flocculant forms. A solvency factor, an asphaltene factor, and a solubility value is calculated from the first and second measured amounts of the aromatic hydrocarbon solvent and the first and second measured amounts of the aliphatic hydrocarbon solvent. Optionally, when the first or second asphaltene flocculant does not form, a concentration of the solid asphaltene-containing deposit in the first and second test samples is altered thereby allowing a first and second asphaltene flocculant to form.

Additionally, disclosed herein is a method for determining a stability of an asphaltene dispersion. The method comprises dissolving a measured amount of a solid asphaltene-containing deposit in a first solvent to form an asphaltene sample, and contacting a first measured amount of the asphaltene sample with a first measured amount of an aromatic hydrocarbon solvent to form a first test sample. A second measured amount of the asphaltene sample is collected and optionally contacted with a second measured amount of the aromatic hydrocarbon solvent to form a second test sample. A first measured amount of an aliphatic hydrocarbon solvent is added to the first test sample until an asphaltene flocculant forms. A second measured amount of the aliphatic hydrocarbon solvent is added to the second test sample until an asphaltene flocculant forms. A solvency factor, an asphaltene factor, and a solubility value is calculated from the first and second measured amounts of the aromatic hydrocarbon solvent and the first and second measured amounts of the aliphatic hydrocarbon solvent. The steps herein are repeated upon adding a solvating agent to the first and second test samples and the solubility value of the samples is compared with the solvating agent to the solubility value of the test samples without the solvating agent. Optionally, when the first or second asphaltene flocculant does not form, a concentration of the solid asphaltene-containing deposit in the first and second test samples is altered to form a first and second asphaltene flocculant.

Further, methods described herein can have the aromatic hydrocarbon solvent comprise toluene, xylene, heavy aromatic distillates, methyl naphthalene, or a combination thereof. Preferably, the aromatic hydrocarbon solvent comprises toluene.

The methods described herein can have the aliphatic hydrocarbon solvent comprises an n-alkane. In particular, the aliphatic hydrocarbon solvent comprises n-pentane, n-hexane, n-heptane, n-octane, iso-octane, nonane, decane, undecane, dodecane, pentadecane, hexadecane, or a combination thereof. Preferably, the aliphatic hydrocarbon solvent comprises iso-octane.

The methods described herein can have the first solvent comprise a mixture of an aliphatic solvent and an aromatic solvent. The aliphatic solvent in the mixture can be n-pentane, n-hexane, n-heptane, n-octane, iso-octane, nonane, decane, undecane, dodecane, pentadecane, hexadecane, or a combination thereof. The aromatic solvent in the mixture can be toluene, xylene, heavy aromatic distillates, methyl naphthalene, or a combination thereof. Preferably, the first solvent comprises n-heptane and toluene.

The methods described herein can also have the second test sample comprise the second measured amount of the asphaltene sample.

The methods can further have the second test sample comprise the second measured amount of the asphaltene sample and a second measured amount of the aromatic hydrocarbon solvent.

The methods disclosed herein can have the asphaltene flocculant be detected by a decrease in light transmission through the test sample.

The methods further can require that when the first asphaltene flocculant is not detected after addition of the aliphatic solvent, the concentration of the asphaltene-containing deposit in the first test sample is increased.

Additionally, the methods can require that when the second asphaltene flocculant is not detected after addition of the aliphatic solvent, the concentration of the asphaltene-containing deposit in the second test sample is increased.

Specifically, the solid asphaltene-containing sample, a solvating agent, and an aromatic solvent are weighed into aluminum tubes in a variety of ratios. For example, the weight ratio of the concentration of the solid asphaltene-containing deposit to the solvating agent is from about 1:4 to about 4:1, from about 1:3 to about 3:1, from about 1:2 to about 2:1, from about 1:1.5 to about 1.5:1, or about 1:1. Preferably, the weight ratio of the concentration of the solid asphaltene-containing deposit to the solvating agent is about 1:1.

Further, the weight ratio of concentrations of the solid asphaltene-containing deposit to the aromatic hydrocarbon solvent is from about 1:8 to about 2:1, from about 1:6 to about 2:1, from about 1:5 to about 2:1, from about 1:4 to about 2:1, from about 1:2 to about 2:1, from about 1:8 to about 1:1, from about 1:6 to about 1:1, from about 1:5 to about 1:1, from about 1:4 to about 1:1, from about 1:2 to about 1:1, 1:8 to about 1:2, from about 1:6 to about 1:2, from about 1:5 to about 1:2, from about 1:4 to about 1:2, or from about 1:3 to about 1:2. Preferably, the weight ratio of concentrations of the solid asphaltene-containing deposit to the aromatic hydrocarbon solvent is from about 1:6 to about 1:2.

In a specific example, the weight ratios can be as follows.

|  | Test Cell 1 | Test Cell 2 |
| --- | --- | --- |
| Sample | 1.25 | 2.50 |
| Solvating Agent | 1.25 | 2.50 |
| Toluene | 7.00 | 5.00 |

The actual weight of each component is weighed in grams to two decimal places. Depending on the asphaltene-containing sample, the relative amounts of the sample, solvating agent, and toluene are changed to obtain an asphaltene flocculant and a corresponding decrease in the optical transmission.

A magnetic stirring bar is added to the aluminum tubes and the tubes are capped with aluminum retaining caps. The tubes are then placed into the stirring hot plate, which is heated to 40° C.-100° C. and stirred at 150-500 rpm. The samples are heated to the set temperature and stirred for from 2-10 minutes to allow for complete dissolution of the solid asphaltene-containing sample.

Once the samples are heated, the aluminum caps are removed and light transmission probes are placed in the aluminum test tubes to detect the precipitation of the asphaltenes.

An aliphatic solvent is added to the aluminum tubes slowly. The light probes are run in transmission mode and the light transmission increases as the sample solution becomes more dilute as additional iso-octane is added. At the point where the asphaltene in the sample forms a flocculant, the light transmission dramatically decreases; this is called the endpoint. Optionally, if this transmission decrease (or endpoint) is not observed at either concentration, or just at the low concentration, then the proportions of sample and solvating agent to toluene are adjusted and the test is run again to see the endpoint at both concentrations.

If clear endpoints are observed in both low and high concentration samples, the titration endpoint is recorded and the Af (asphaltene factor), Sf (solvency factor) and SV (Stability Value) are calculated.

A more efficacious solvating agent is evidenced by improvements in Af and Sf and an increase in the overall dispersion stability (SV).

Additionally, an asphaltene sample prepared by using a selected asphaltene-containing solid sample dissolved in a first solvent (e.g., an aromatic-aliphatic solvent) can be prepared. Desirably, this asphaltene sample has a similar solvency power as compared to the tested crude oil. Typically, the concentration of the asphaltene-containing solid sample in the asphaltene sample does not exceed 10% wt.

The asphaltene-containing solid sample is well dissolved in the first solvent by using heat and stirring for from one to five hours at from 50° C.-100° C.

The asphaltene-containing solid sample and aromatic solvent are weighed into the aluminum tubes using a variety of ratios. For example, the concentration of the solid asphaltene-containing deposit is from about 0.1 wt. % to about 50 wt. %, from about 0.1 wt. % to about 40 wt. %, from about 0.1 wt. % to about 30 wt. %, from about 0.1 wt. % to about 20 wt. %, from about 0.1 wt. % to about 15 wt. %, from about 0.25 wt. % to about 50 wt. %, from about 0.25 wt. % to about 40 wt. %, from about 0.25 wt. % to about 30 wt. %, from about 0.25 wt. % to about 20 wt. %, from about 0.25 wt. % to about 15 wt. %, from about 0.5 wt. % to about 50 wt. %, from about 0.5 wt. % to about 40 wt. %, from about 0.5 wt. % to about 30 wt. %, from about 0.5 wt. % to about 20 wt. %, or from about 0.5 wt. % to about 15 wt. % in the amphiphilic solvent, based on the total weight of the solid asphaltene-containing deposit and the amphiphilic solvent. Preferably, the concentration of the asphaltene-containing solid sample is from about 5 wt. % to about 10 wt. % in the amphiphilic solvent.

Additionally, the weight ratio of the concentrations of the asphaltene sample to the aromatic solvent is from about 20:1 to about 1:1.

Specifically, the weights of the asphaltene sample and the aromatic solvent (e.g., toluene) can be as follows.

|  | Test Cell 1 | Test Cell 2 |
| --- | --- | --- |
| Sample | 7.00 | 10.00 |
| Toluene | 3.00 | 0.00 |

The actual weights of the asphaltene sample and the aromatic solvent (e.g., toluene) are recorded to two decimal places. The concentrations of the asphaltene sample and aromatic solvent (e.g., toluene) are adjusted if the precipitation of the asphaltene deposit and the corresponding decrease in transmission is not observed at the measured concentrations.

The magnetic stirring bar is added to the tubes and the aluminum tubes are capped. The tubes are then placed into the stirring hot plate, heated to 40° C.-100° C. and stirred at 150-500 rpm. The samples are heated to the set temperature and heated and stirred for 2-10 minutes After heating the samples, the aluminum caps are removed and the light probe is placed into the aluminum test tube.

Iso-octane is added to the aluminum tubes slowly. The light probes are run in transmission mode and the light transmission increases as the sample solution becomes more dilute with additional iso-octane added. At the point where the asphaltene in the sample forms a flocculant, the light transmission dramatically decreases; this is called the endpoint. Optionally, if this transmission decrease (or endpoint) is not observed at either concentration, or just at the low concentration, then the proportions of sample and solvating agent to toluene are adjusted and the test is run again to see the endpoint at both concentrations.

If clear endpoints are observed in both low and high concentration samples, the titration endpoint is recorded and the Af (asphaltene factor), Sf (solvency factor) and SV (Stability Value) are calculated.

The test is repeated with various solvating agents and concentrations to discover their interaction with the asphaltene fraction, which can be observed by improvements in Af and Sf and an increase in the overall dispersion stability (SV).

A refined method for selecting a solvating agent system considers both the asphaltene solubility kinetics (i.e., inhibition) and the asphaltene concentration per unit volume (i.e., dispersancy) The ability to disperse asphaltenes in solution is an important parameter that enables more asphaltenic material to be retained per unit volume fluid and therefore reduces the risk of re-deposition during various procedures, e.g., soak and flowback procedures. The assessment of solubility uses the methods described herein by preparing mixtures of a field deposit and a solvating agent at a 1:1 ratio and mixing the resulting solution with heptane at a 20% v/v oil dilution. The solution is then thoroughly mixed and placed in a stability analyzer as described in Examples 1 and 2 to measure flocculation and sedimentation under accelerated gravity conditions. Sedimentation profiles are recorded by NIR light transmission changes over time.

To assess which asphaltene solvating agents have the capacity to dissolve more asphaltenic material per unit volume than a standard solvent (e.g. xylene), the whole NIR transmission spectrum for each solution is examined. Essentially, the greater the mass of asphaltenic material dissolved per unit volume of solvent correlated to a higher fluid density. As density and other physical properties of a hydrocarbon fluid can be correlated with NIR spectroscopy, a NIR immersion transmission probe is used to examine the spectra of the samples. The larger the mass of asphaltenic material dissolved per unit volume of solvent, the lower the transmission of NIR light. The same sample concentrations are used as before (1:1 ratio of deposit to sample), and the spectra are measured from a known volume.

The difference between the transmission spectra for samples having solvent only or a solvent and a solvating agent show that highly effective solvating agents allow far less NIR light to pass through the same as compared to the sample containing solvent only. The data provide further evidence to support the theory that specifically designed products based on field deposit asphaltene interactions, can break down the deposit to the smallest constituents, and keep them dispersed in solution and allow more material to be packed in per unit volume of fluid (i.e., resulted in an increase in density of the solution).

The experience of developing and applying the test methods described above to the design and selection of effective and high efficiency solvating agents or remediation products also influences the development and screening of potential continuous application asphaltene products. Working with a specific field asphaltene deposit, it is possible to rapidly screen many products and components to identify a solution most appropriate to the problematic asphaltenes for that field.

As used herein, the term "asphaltene" refers to a class of hydrocarbons in carbonaceous material, such as crude oil, bitumen, or coal that is soluble in toluene, xylene, and benzene, yet insoluble in n-alkanes, e.g., n-heptane and n-pentane. Asphaltenes are generally characterized by fused ring aromaticity with some small aliphatic side chains, and typically some polar heteroatom-containing functional groups, e.g., carboxylic acids, carbonyl, phenol, pyrroles, and pyridines, capable of donating or accepting protons intermolecularly and/or intramolecularly, having a molar H/C ratio of about 1 to 1.2, and a N, S, and O content of a low weight percent.

As used herein, the term "precipitation propensity" refers to the tendency of a composition that includes a first crude oil or a composition that includes a first crude oil and at least one second crude oil to precipitate asphaltenes, where at least one of the first crude oil and the second crude oil includes asphaltenes. The precipitation propensity can be measured by any conventional technique for measuring asphaltene precipitation or aggregation, including, but not limited to, volumetric solvent titrimetry with optical measurement, e.g., infrared spectroscopy and/or near infrared spectroscopy, including oil compatibility models; Asphaltene Stability Index (ASI) test using solvent-titration, as described in Gawrey, et al., *Instrumentation Science & Technology*, 2004, 32(3), 247-253; solvent titrimetry with electrical measurement, e.g., conductivity and/or capacitance, as described in U.S. Pat. No. 5,420,040; solvent titrimetry with surface tension measurement, as described in U.S. Pat. No. 5,420,040; spot testing, as described in ASTM E 4740 (2004); viscometry, as described in J. Escobedo, et al., "Viscometric Determination of the Onset of Asphaltene Flocculation: A Novel Method," *Society of Petroleum Engineers*, May 1995; optical microscopy; refractive indices measurement, as described in ASTM E 1218 (2012); vapor pressure osmometry, as described in U.S. Pat. No. 5,420,040 and Gawrey, et al., *Instrumentation Science & Technology*, 2004, 32(3), 247-253); gravimetric titrimetry, as described in U.S. Pat. No. 5,420,040; autoclaving; colloidal instability index, as described in Gawrey, et al., *Instrumentation Science & Technology*, 2004, 32(3), 247-253; detection of bubble points and asphaltene aggregation onset pressures by NIR, as described by Aske, et al., *Energy & Fuels*, 2002, 16, 1287-1295; nuclear magnetic resonance (NMR) relaxometry, as described in Prunelet et al., C. R. *Chimie* 7 (2004); pulsed-field gradient spin echo nuclear magnetic resonance (NMR), as described in Gawrey, et al., *Instrumentation Science & Technology*, 2004, 32(3), 247-253; small-angle neutron scattering, as described in Gawrey, et al., *Instrumentation Science & Technology*, 2004, 32(3), 247-253; saturates, asphaltenes, resins, aromatics (SARA) analysis, where NR>0.35 is unstable, as described in Falkler et al., *Hydrocarbon Processing*, September 2010, 67-73; or any combination thereof.

As used herein, the term "solubility ratio" refers to a precipitation propensity of a crude oil determined by: (i) adding an asphaltene non-solvent to an initial volume of a crude oil; (ii) measuring the volume of the asphaltene non-solvent that causes asphaltene precipitation, e.g., by determining a minimum optical density as measured by near infrared spectroscopy; and (iii) dividing the volume of the asphaltene non-solvent added to the crude oil by the initial volume of the crude oil.

As used herein, the term "near-infrared spectrometry" or "NIR spectrometry" refers to spectroscopic methods that use the near-infrared region of the electromagnetic spectrum from about 800 nm to about 2,500 nm. The methods discussed and described herein can be used to predict the compatibility of a wide range of different crude oils before blending, including operable proportions, to reduce, minimize, prevent, or eliminate asphaltene precipitation and/or one or more of the problems caused by asphaltene precipitation such as unplanned refinery events caused by asphaltene precipitation. The proportions of any number of crude oils in a blend and/or to be combined with one another to form a blend can also be determined to help optimize crude rate and/or crude blend compatibility. The methods and the associated calculations allow a precipitation propensity, such as a solubility ratio as measured by near-infrared spectrometry, to be determined for the crude oil blend components.

As used herein, the term "optical density" (i.e., OD) refers to the attenuated measurement in the incident light due to absorbance and scattering by a medium through which the light travels. Asphaltenes can flocculate from solution with the addition of an asphaltene non-solvent, e.g., an n-alkane such as n-heptane, and the OD can be affected by the flocculation of the asphaltenes. The optical density at a wavelength of about 1,600 nm can be of particular interest since it corresponds to a region associated with relatively low background absorbance for crude oil. As asphaltene nonsolvent is added to a crude oil sample (also referred to as "titration"), the NIR absorbance and the OD at about 1,600 nm decrease initially due to dilution of the sample; however, asphaltene flocculation causes an increase in the OD as the transmitted light is reduced due to the scattering and absorbance of light by the flocculated asphaltenes. Hence, a minimum is observed in the OD at about 1,600 nm with addition of an asphaltene non-solvent such as n-heptane. It is the volume of asphaltene non-solvent corresponding to the minimum OD that is reported as the onset point of asphaltene flocculation and used in the solubility ratio.

Having described the invention in detail, it will be apparent that modifications and variations are possible without departing from the scope of the invention defined in the appended claims.

EXAMPLES

The following non-limiting examples are provided to further illustrate the present invention.

Example 1: Dispersion Stability Parameters

The solid asphaltene-containing sample, a solvating agent, and toluene were weighed into aluminum tubes to achieve the following amounts. The actual weight of each component was weighed in grams to 2 decimal places. Depending on the asphaltene-containing sample, the relative amounts of the sample, solvating agent, and toluene were changed to provide a sample that resulted in the asphaltene precipitating after addition of an aliphatic solvent.

|  | Test Cell 1 | Test Cell 2 |
| --- | --- | --- |
| Sample | 1.25 | 2.50 |
| Solvating Agent | 1.25 | 2.50 |
| Toluene | 7.00 | 5.00 |

A two channel Residual Stability Analyzer (RSA) instrument included test cells, a titrant dispenser system, and an optic probe-detector system. The test cells were rugged, tapered, anodized aluminum cylinders (about 90 mL volume) that allowed for rapid heat transfer for rapid heating and cooling. During the test procedure these cells were located in two aluminum "heat sink" cell holders beneath which magnetic stirrers were located to facilitate sample/titrant mixing.

The two fiber optic probes were constructed from aluminum and silver bronze head housing mirrored light guide quartz prisms. The probes operated in transmission mode and had a cell path-length of 0.4 mm. The light source was a 960 nm NIR VCSEL.

Titrant (Iso-octane) was dispensed into the test cylinders by means of two high accuracy micro dosing pumps. The pumps were capable of delivering titrant at rates of from 0.1 mL/minute to 5 mL/minute. Under normal operation the titrant rate was fixed at 2 mL/minute, and pre-calibrated using the instrument's software.

A magnetic stirring bar was added to the aluminum tubes and the tubes were capped with aluminum retaining caps. The tubes were then placed into the stirring hot plate, which was set to 55° C. and 300 rpm. The samples were heated to the set temperature and stirred for 5 minutes to allow for complete dissolution of the solid sample.

Once the samples were heated, the aluminum caps were removed and light probes were placed in the aluminum test tubes to detect the precipitation of the asphaltenes.

Iso-octane was added to the aluminum tubes slowly. The light probes were run in transmission mode and the light transmission increased as the sample solution became more dilute with additional iso-octane added. At the point where the asphaltene in the sample formed a flocculant, the light transmission dramatically decreased, this was called the endpoint. If this transmission decrease (or endpoint) was not observed at either concentration, or just at the low concentration, then the proportions of sample and solvating agent to toluene were adjusted and the test was run again to see the endpoint at both concentrations.

If clear endpoints were observed in both low and high concentration samples, the titration endpoint was recorded and the Af (asphaltene factor), Sf (solvency factor) and NSV (Nalco Stability Value) were calculated.

A more efficacious solvating agent can be observed by improvements in Af and Sf that promote an increase in the overall dispersion stability (NSV).

Example 2: Asphaltene Inhibitor Performance

A stock solution of an asphaltene sample (i.e., model oil) was made using the selected asphaltene-containing solid sample and a heptol, or other aromatic-aliphatic hydrocarbon solvent, to prepare a mixture that has a similar solvency power as compared to the tested crude oil. Typically, the concentration of the asphaltene-containing solid sample in the model oil did not exceed 10% wt.

The asphaltene-containing solid sample was well dissolved in the heptol by using heat and stirring for a minimum of one hour at 60° C.

The model oil and toluene were weighed into the aluminum tubes using the following approximate concentrations. The actual weights of the model oil containing the sample and the toluene were recorded to two decimal places. The concentrations of the model oil and toluene were adjusted if the decrease in transmission was not observed at the measured concentration.

|  | Test Cell 1 | Test Cell 2 |
| --- | --- | --- |
| Sample | 7.00 | 10.00 |
| Toluene | 3.00 | 0.00 |

The magnetic stirring bar was added to the tubes and the aluminum tubes were capped. The tubes were then placed into the stirring hot plate, heated to 55° C. and stirred at 300 rpm. The samples were heated to the set temperature and heated and stirred for at least five minutes After heating the samples, the aluminum caps were removed and the light probe was placed into the aluminum test tube.

Iso-octane was added to the aluminum tubes slowly. The light probes were run in transmission mode and the light transmission increased as the sample solution became more dilute with additional iso-octane added. At the point where the asphaltene in the sample formed a flocculant, the light transmission dramatically decreased, this was called the endpoint. If this transmission decrease (or endpoint) was not observed at either concentration, or just at the low concentration, then the proportions of sample and solvating agent to toluene were adjusted and the test was run again to see the endpoint at both concentrations.

If clear endpoints were observed in both low and high concentration samples, the titration endpoint was recorded and the Af (asphaltene factor), Sf (solvency factor) and SV (Stability Value) were calculated.

The test was repeated with various solvating agents and concentrations to discover their interaction with the asphaltene fraction, which may be observed by improvements in Af and Sf and an increase in the overall dispersion stability (SV).

Figure 1:
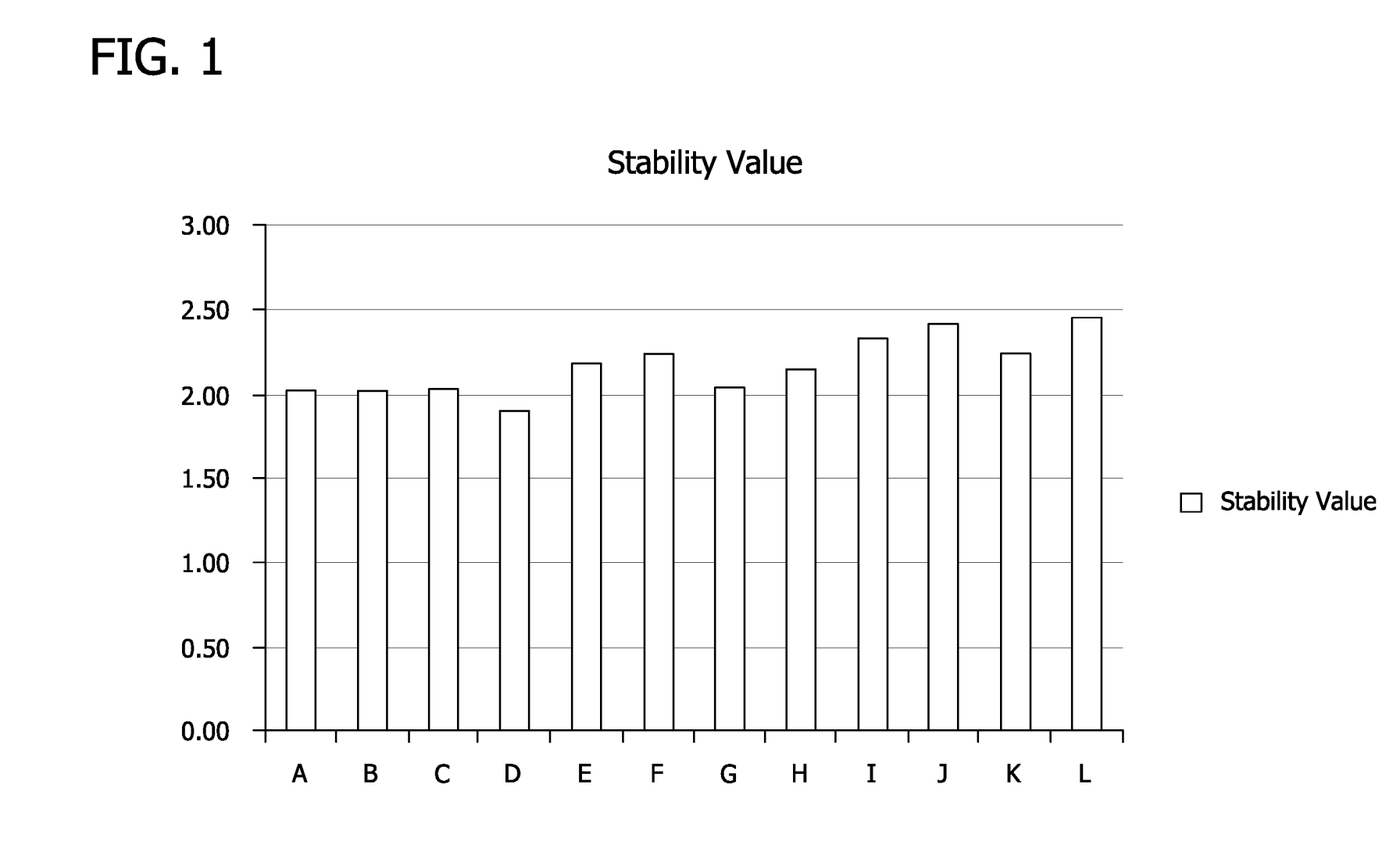
FIG. 1 is a graph of the relative solubility ranking for solvating agents.

For example, FIG. 1 shows the results of this test for toluene (Product A), xylene (Product B), 5% Dispersant A in xylene (Product C), dipentene rich terpentine oil (Product D), heavy aromatic naphtha (HAN) (Product E), 10% v/v Dispersant B in HAN (Product F), 5% v/v Dispersant A in HAN (Product G), 5% v/v Dispersant C in HAN (Product H), 5% v/v Dispersant D in HAN (Product I), 10% v/v Dispersant D in HAN (Product J), 5% v/v Dispersant E in HAN (Product K), and 5% v/v Dispersant D and 5% v/v Dispersant E in HAN (Product L).

Example 3: Selection of Solvating Agent

Asphaltene Solubility. The ability to disperse asphaltenes in solution is an important parameter that enables more asphaltenic material to be retained per unit volume fluid and therefore reduces the risk of re-deposition during various procedures, e.g., soak and flowback procedures. The assessment of solubility was obtained by preparing mixtures of field deposit and solvating agents at a 1:1 ratio and mixing the resulting solution with heptane at a 20% v/v oil dilution. The solution was then thoroughly mixed and placed in a stability analyzer as described in Examples 1 and 2 to measure flocculation and sedimentation under accelerated gravity conditions. Sedimentation profiles were recorded by NIR light transmission changes over time.

Asphaltene Concentration. To assess which asphaltene solvating agents had the capacity to dissolve more asphaltenic material per unit volume than a standard solvent (e.g. xylene), the whole NIR transmission spectrum for each solution was examined. Essentially, the greater the mass of asphaltenic material dissolved per unit volume of solvent correlated to a higher fluid density. As density and other physical properties of a hydrocarbon fluid can be correlated with NIR spectroscopy, a NIR immersion transmission probe was used to examine the spectra of the samples. The larger the mass of asphaltenic material dissolved per unit volume of solvent, the lower the transmission of NIR light. The same sample concentrations were used as before (1:1 ratio of deposit to sample), and the spectra measured from a known volume.

The transmission spectra for samples having solvent only or a solvent and a solvating agent were clearly different; highly effective solvating agents allowed far less NIR light to pass through the same as compared to the sample containing solvent only. The data provided further evidence to support the theory that specifically designed products based on field deposit asphaltene interactions, can break down the deposit to the smallest constituents, and keep them dispersed in solution and allowed more material to be packed in per unit volume of fluid (i.e., resulted in an increase in density of the solution).

The experience of developing and applying the test methods described above to the design and selection of effective and high efficiency solvating agents or remediation products also influenced the development and screening of potential continuous application asphaltene products. Working with a specific field asphaltene deposit, it was possible to rapidly screen many products and components to identify a solution most appropriate to the problematic asphaltenes for that field.

The assessment of product performance was based on the determination of asphaltene solubility kinetics and the asphaltene concentration per unit volume fluid. The first test provided a measure of inhibition potential, i.e., the ability of asphaltenic material to remain stabilized over time. The second test indicated the dispersion potential, as products that can break down and disperse asphaltenic material will generate a relatively denser fluid. Using these two parameters, a performance map based on dispersion and inhibition was constructed. An example for a particular field deposit is displayed in FIG. 2.

Figure 2:
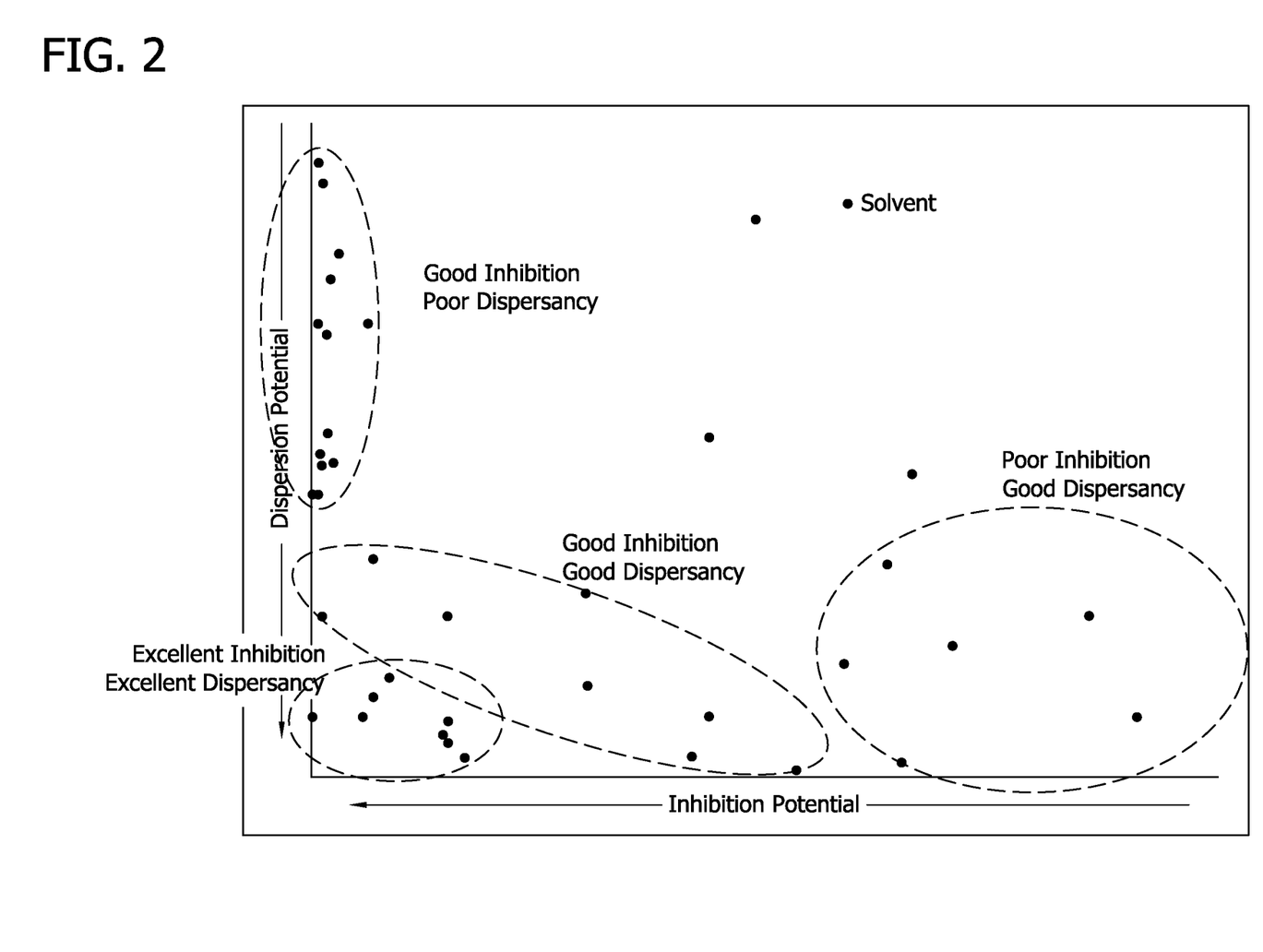
FIG. 2 is a graph of the inhibition potential versus the dispersion potential for various solvating agents.

Each data point represents a distinct product formulation of the solvating agents. Pure solvent resides toward the top right of the map, suggesting that it has neither dispersant or inhibitor properties. Certain products are good dispersants, but poor inhibitors, and vice versa. However, some products displayed each property, and these were the products of interest. Significantly, when examined on sophisticated pseudo-live-oil depressurization tests, such as Nalco Champion's Asphaltene Rocking Cell, these products performed very well. The test therefore permits rapid screening of many products prior to detailed examination under the rocking cell environment.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

The invention claimed is:

1. A method for determining a stability of an asphaltene dispersion, the method comprising
dissolving a measured amount of a solid asphaltene-containing deposit in a first solvent to form an asphaltene sample,
contacting a first measured amount of the asphaltene sample with a first measured amount of an aromatic hydrocarbon solvent to form a first test sample;
collecting a second measured amount of the asphaltene sample and optionally contacting it with a second measured amount of the aromatic hydrocarbon solvent to form a second test sample;
adding a first measured amount of an aliphatic hydrocarbon solvent to the first test sample until an asphaltene flocculant forms;
adding a second measured amount of the aliphatic hydrocarbon solvent to the second test sample until an asphaltene flocculant forms;
calculating a solvency factor, an asphaltene factor, and a solubility value from the first and second measured amounts of the aromatic hydrocarbon solvent and the first and second measured amounts of the aliphatic hydrocarbon solvent; and
repeating the steps herein upon adding a solvating agent to the first and second test samples and comparing the solubility value of the samples with the solvating agent to the solubility value of the test samples without the solvating agent.

2. The method of claim 1, wherein when the first or second asphaltene flocculant does not form, a concentration of the solid asphaltene-containing deposit in the first and second test samples is altered thereby allowing a first and second asphaltene flocculant to form.

3. The method of claim 1, wherein the first solvent comprises a mixture of an aliphatic solvent and an aromatic solvent.

4. The method of claim 3, wherein the aliphatic solvent in the first solvent comprises n-pentane, n-hexane, n-heptane, n-octane, iso-octane, nonane, decane, undecane, dodecane, pentadecane, hexadecane, or a combination thereof.

5. The method of claim 3, wherein the aromatic solvent in the first solvent comprises toluene, xylene, heavy aromatic distillates, methyl naphthalene, or a combination thereof.

6. The method of claim 3, wherein the first solvent comprises n-hexane and toluene.

7. The method of claim 1, wherein the concentration of the solid asphaltene-containing deposit is from about 0.5 wt. % to about 15 wt. % in the amphiphilic solvent, based on the total weight of the solid asphaltene-containing deposit and the amphiphilic solvent.

8. The method of claim 7, wherein the ratio of the concentrations of the asphaltene sample to the aromatic solvent is from about 20:1 to about 1:1.

9. The method of claim 8, wherein the second test sample comprises the second measured amount of the asphaltene sample and a second measured amount of the aromatic hydrocarbon solvent.

10. A method for determining an asphaltene concentration per unit volume of fluid, the method comprising
contacting a first measured amount of a solid asphaltene-containing deposit with a first measured amount of a solvating agent and a first measured amount of an aromatic hydrocarbon solvent to form a first test sample of a specific volume;
contacting a second measured amount of the solid asphaltene-containing deposit with a second measured amount of the aromatic hydrocarbon solvent to form a second test sample;
allowing the solid asphaltene-containing deposit to dissolve in the solvating agent and aromatic hydrocarbon solvent or in the aromatic hydrocarbon solvent to form a solution in each of the first and the second test samples;
measure the transmission of the first and the second test samples using a near infrared (NIR) probe; and
compare the NIR spectra of the first test sample to the second test sample wherein a lower transmission of NIR light indicates a higher mass of asphaltene-containing deposit in the sample.

11. The method of claim 10, wherein the aromatic hydrocarbon solvent comprises toluene, xylene, heavy aromatic distillates, methyl naphthalene, or a combination thereof and the ratio of the concentration of the solid asphaltene-containing deposit to the solvating agent is from about 1:4 to about 4:1.

12. The method of claim 1, further comprising comparing the solubility value of different solvating agents.

13. The method of claim 10, further comprising comparing the mass of asphaltene-containing deposit in the sample comprising different solvating agents.

14. A method for comparing the solubility value of different solvating agents and the dispersion ability of different solvating agents, the method comprising
(a) dissolving a measured amount of a solid asphaltene-containing deposit in a first solvent to form an asphaltene sample,
contacting a first measured amount of the asphaltene sample with a first measured amount of an aromatic hydrocarbon solvent to form a first test sample;
collecting a second measured amount of the asphaltene sample and optionally contacting it with a second measured amount of the aromatic hydrocarbon solvent to form a second test sample;
adding a first measured amount of an aliphatic hydrocarbon solvent to the first test sample until an asphaltene flocculant forms;
adding a second measured amount of the aliphatic hydrocarbon solvent to the second test sample until an asphaltene flocculant forms;
calculating a solvency factor, an asphaltene factor, and a solubility value from the first and second measured amounts of the aromatic hydrocarbon solvent and the first and second measured amounts of the aliphatic hydrocarbon solvent; and
repeating the steps herein upon adding a solvating agent to the first and second test samples and comparing the solubility value of the samples with the solvating agent to the solubility value of the test samples without the solvating agent; and
comparing the solubility values of different solvating agents; and
(b) contacting a first measured amount of a solid asphaltene-containing deposit with a first measured amount of a solvating agent and a first measured amount of an aromatic hydrocarbon solvent to form a first test sample of a specific volume;
contacting a second measured amount of the solid asphaltene-containing deposit with a second measured amount of the aromatic hydrocarbon solvent to form a second test sample;
allowing the solid asphaltene-containing deposit to dissolve in the solvating agent and aromatic hydrocarbon solvent or in the aromatic hydrocarbon solvent to form a solution in each of the first and the second test samples;
measure the transmission of the first and the second test samples using a near infrared (NIR) probe; and
compare the NIR spectra of the first test sample to the second test sample wherein a lower transmission of NIR light indicates a higher mass of asphaltene-containing deposit in the sample; and
comparing the mass of asphaltene-containing deposit in the sample comprising different solvating agents.

15. The method of claim 14, wherein when the first or second asphaltene flocculant does not form, a concentration of the solid asphaltene-containing deposit in the first and second test samples is altered thereby allowing a first and second asphaltene flocculant to form.

16. The method of claim 14, wherein the first solvent comprises a mixture of an aliphatic solvent and an aromatic solvent.

17. The method of claim 16, wherein the aliphatic solvent in the first solvent comprises n-pentane, n-hexane, n-heptane, n-octane, iso-octane, nonane, decane, undecane, dodecane, pentadecane, hexadecane, or a combination thereof.

18. The method of claim 16, wherein the aromatic solvent in the first solvent comprises toluene, xylene, heavy aromatic distillates, methyl naphthalene, or a combination thereof.

19. The method of claim 16 wherein the first solvent comprises n-hexane and toluene.

20. The method of claim 14, wherein the aromatic hydrocarbon solvent comprises toluene, xylene, heavy aromatic distillates, methyl naphthalene, or a combination thereof and the ratio of the concentration of the solid asphaltene-containing deposit to the solvating agent is from about 1:4 to about 4:1.

* * * * *

UNITED STATES PATENT AND TRADEMARK OFFICE
CERTIFICATE OF CORRECTION

| | | |
|---|---|---|
| PATENT NO. | : 11,280,779 B2 | Page 1 of 1 |
| APPLICATION NO. | : 16/224290 | |
| DATED | : March 22, 2022 | |
| INVENTOR(S) | : Russell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 578 days.

Signed and Sealed this
Eighteenth Day of February, 2025

Coke Morgan Stewart
*Acting Director of the United States Patent and Trademark Office*